United States Patent [19]

Berta

[11] Patent Number: 5,436,026
[45] Date of Patent: Jul. 25, 1995

[54] DISCHARGE AND TRANSFER SYSTEM FOR APPARATUS FOR GELATIN COATING TABLETS

[75] Inventor: Norbert I. Berta, Devon, Pa.
[73] Assignee: McNeil-PPC, Inc., Milltown, N.J.
[21] Appl. No.: 3,348
[22] Filed: Jan. 12, 1993

Related U.S. Application Data

[63] Continuation-in-part of Ser. No. 609,482, Nov. 5, 1990, Pat. No. 5,228,916.

[51] Int. Cl.$^6$ .................. A61K 9/28; B05C 3/18; B05C 13/00; B05C 21/00
[52] U.S. Cl. .................. 427/2.14; 427/2.22; 118/16; 118/20; 118/30; 118/58; 118/425; 118/426; 118/500; 118/503; 414/404
[58] Field of Search .................. 118/16, 20, 30, 58, 118/425, 426, 500, 503; 427/3, 2.14, 2.22; 414/404, 417, 222, 783

[56] References Cited

U.S. PATENT DOCUMENTS

| | | | |
|---|---|---|---|
| 3,453,989 | 7/1969 | Bippus | 118/503 |
| 3,844,428 | 10/1974 | Olsen | 414/417 |
| 3,896,762 | 7/1975 | Banker | 118/30 |
| 4,526,129 | 7/1985 | Braden | 118/503 |
| 4,532,881 | 8/1985 | Sakashita et al. | 118/30 |
| 4,669,416 | 6/1987 | Delgado et al. | 118/503 |
| 4,820,524 | 4/1989 | Berta | 424/474 |
| 4,867,983 | 9/1989 | Berta | 118/30 |
| 4,921,108 | 5/1990 | Berta | 209/625 |
| 4,940,499 | 7/1990 | Lebrun et al. | 427/3 |
| 4,965,089 | 10/1990 | Sauter et al. | 427/3 |
| 4,966,771 | 10/1990 | Berta | 118/30 |
| 4,990,358 | 2/1991 | Berta | 427/3 |
| 5,102,287 | 4/1992 | Johnson et al. | 414/618 |
| 5,228,916 | 7/1993 | Berta | 118/30 |
| 5,234,099 | 10/1993 | Berta | 198/803.1 |
| 5,314,537 | 5/1994 | Berta | 118/30 |

FOREIGN PATENT DOCUMENTS

| | | | |
|---|---|---|---|
| 271627 | 6/1988 | European Pat. Off. | 118/20 |
| 0448231A1 | 9/1991 | European Pat. Off. | |
| 2434803 | 2/1975 | Germany | 118/30 |

Primary Examiner—W. Gary Jones
Assistant Examiner—Steven P. Griffin
Attorney, Agent, or Firm—Bernard F. Plantz

[57] ABSTRACT

Apparatus and method for coating products with two colors including a first coating section, a second coating section and a side to side transfer device for transferring products from the first to the second sections. The transfer device includes a pair of plate grippers each having a movable upper jaw and a movable lower jaw. The upper and lower jaws are each adapted to receive and retain a product carrier plate. The transfer device includes a cam follower that precisely closes the upper and lower jaws so that carrier plates located in the jaws are positioned in registration with each other in order to clamp product between the plates and to maintain the product clamped in the plates while the grippers are transferred between the first and second conveyor guides. An unloading station includes breaker pins for breaking a seal that may be formed between the coating material applied in the first coating section and the carrier plates. At a discharge station the carrier plates are rotated to cause the product to fall to a collection bin. Clean out bars adapted to be extended through the carrier plates while the plates are in the rotated discharge position cause any product that may have adhered to the plate and any excess coating material on the plate to be removed.

22 Claims, 15 Drawing Sheets

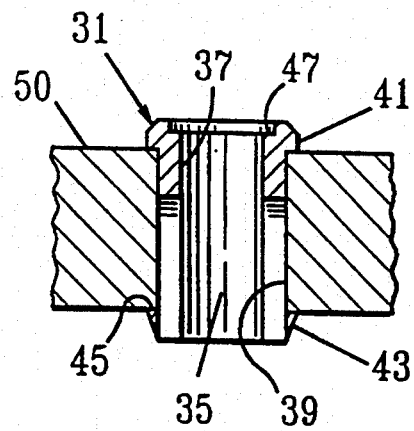
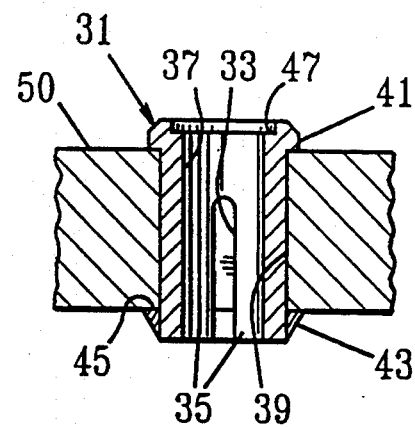
FIG. 7A  FIG. 7B
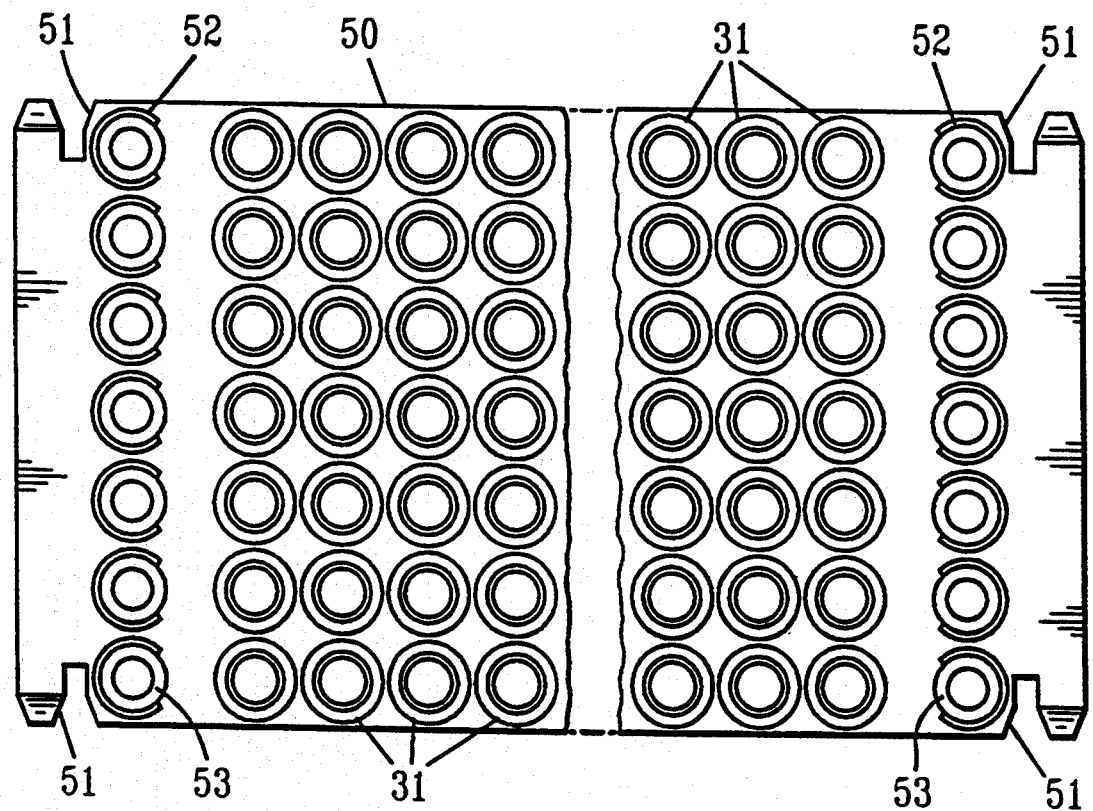
FIG. 8

DISCHARGE AND TRANSFER SYSTEM FOR APPARATUS FOR GELATIN COATING TABLETS

This application is a continuation-in-part application of my application Ser. No. 609,482, filed Nov. 5, 1990 entitled Methods and Apparatus for Creating a Gelatin Coating, now U.S. Pat. No. 5,228,916, which is commonly assigned and which is hereby incorporated by reference as if fully set forth herein.

The present invention relates to methods and apparatus for forming a coating on a product and, more particularly, to methods and apparatus for forming a coating comprised of a gelatinous substance on a tablet. The present invention further relates to methods and apparatus for providing at least two different coatings to a tablet in a duplex system.

The present invention is related to my prior patents U.S. Pat. Nos. 4,921,108 issued on May 1, 1990; 4,867,983 issued on Sep. 19, 1989; 4,820,524 issued on Apr. 11, 1989 and 4,966,771 issued on Oct. 30, 1990, and my U.S. patent application Ser. No. 483,154, filed Feb. 22, 1990, now U.S. Pat. No. 5,234,099, which is assigned to the same assignee as the present application and incorporated by reference as if fully set forth herein.

The present invention is also related to my U.S. patent applications, Ser. Nos. 08/023,151, 08/023,334, 08/023,347 and 08/023,349 all filed concurrently herewith, which are all assigned to the assignee of the present application and incorporated by reference as if fully set forth herein.

BACKGROUND OF THE INVENTION

Many products, from prescription drugs to commonly available vitamin tablets to candy, are manufactured in a form which may be described as a "tablet." The primary function of a tablet is to provide a single dose or "serving" of the product in a manner which is convenient to manufacture, package and consume. As pointed out in my previous patents and applications, referenced above, it has been found that certain individuals suffer from physiological and psychological problems which impede their ability to swallow tablets. It has also been found that by providing tablets with a smooth coating, such as a coating comprised of gelatin or a gelatinous substance that the "swallowability" of a tablet is greatly enhanced. Such coatings and the general considerations involved in their application, such as preparation and drying time, are well known to those of ordinary skill.

In addition to enhanced swallowability, there are numerous other reasons that it is desirable to provide a coating on a tablet. Such coatings protect the underlying product from deterioration and also serve to permit identifying colors or markings to be incorporated onto the design of the product, promoting product differentiation and brand identification. As pointed out in my previous patents and applications, it is also desirable in some instances to overlap two or more coatings to form a seam, thereby simulating the appearance of a hard gelatin capsule while providing a coated, solid (and thus tamper resistant) product. Methods and apparatus for applying a gelatinous coating or other coating to a product which is in the form of a tablet are well known to those of ordinary skill. Such methods may include pan dipping or vacuum spraying of the coating material on to the tablet. Such methods are crude, however, producing uneven coatings which are generally unacceptable for commercial use. In an effort to improve the state of the art, the inventions disclosed by my previous patents and applications have provided methods and apparatus whereby individual products are held partially within a sleeve or "collet" and the exposed portion of the product precisely lowered into a dipping tank. As disclosed, bars or plates containing a plurality of product to be dipped are conveyed and rotated and the product itself is manipulated to provide even coatings of high quality and consistency at high volume. These inventions, however, do not permit every type of product such as certain styles of tablets and medicaments to be coated—or at least to be coated in a particular manner. For example, dipping the circular face of a substantially cylindrical tablet whose height is relatively small compared to its diameter would be difficult using the apparatus disclosed by my prior patents and applications, particularly if a circumferential seam is desired. Other examples include the difficulty of coating either a fragile product or applying fragile coating compositions. It has been found that certain coatings will be marred by the friction fit within the collets or similar retaining devices making these unsuitable for use in the apparatus of my prior inventions.

It is known to transport individual tablets or capsules through an immersion coating bath by retaining the tablets on individual vacuum tubes. For example, U.S. Pat. No. 3,896,762—Banker discloses a rotary coating apparatus for pharmaceutical solid dosage forms. Since the surface of the coating is horizontal it is tangential to the path of the tablet; accordingly, Banker discloses that it is necessary to rotate the vacuum tube holding the tablet around its longitudinal axis to achieve an even coating. There are, however, a number of practical shortcomings in the apparatus disclosed. First, although a dryer and ejector are disclosed, the overall system does not lend itself to high volume production or provide for modifications in drying time or inspection, etc. Secondly, the system disclosed by Banker is directed to passing one-half or more of the total depth dimension of the tablet through the coating solution. The tablet is then randomly ejected, with no provision being made to align or otherwise control the orientation of the tablet and the uncoated portion, if any, which exists. Moreover, there is no provision for adjusting the coating to achieve multi-colored or capsule-like coated products. Therefore, one of ordinary skill will appreciate that the system disclosed by Banker is of limited use in current manufacturing environments, where high volume and flexibility are important, along with the need for consistency and high quality.

Therefore, there exists a need for methods and apparatus which can consistently place a precisely defined amount of coating material on an individual product. Such methods and apparatus should be capable of producing coated products at high volume and should possess inherent flexibility to permit new designs and types of coatings to be incorporated without an undue degree of retooling.

SUMMARY OF THE INVENTION

These and other objects of the present invention are achieved by apparatus comprising a conveyor for transporting a plurality of carrier plates having product holders to various processing stations. The processing stations include tablet loading, dipping and drying, which permits the products to be coated in a highly controlled manner. The apparatus also permits two or more colors or types of coatings to be placed on the product. To provide two coatings, a coating is applied to a first portion of the product and then the product is inverted and placed in a second plate so that the uncoated portion may be coated.

One embodiment of an apparatus for coating products with two colors includes a first coating section, a second coating section and a means for transferring products from the first to the second sections. The first section includes a feeding and loading means for depositing products onto the product holders. The product is advanced along a first conveyor guide to a first dipping means that dips the products to coat a first portion of the product. The plates are then advanced to a first rotating means that rotates the plates one revolution for spreading the coating over the first portion. The plates are advanced to a dryer that extends over the first section of the coating apparatus. The plates traverse through the dryer in a controlled manner for curing the coating. The plates are then returned to the conveyor guide where they are advanced to a side to side transfer apparatus. The plates are transferred to the second section of the coating apparatus in such a manner to expose the uncoated portion of the tablets. The plates are then advanced to identical dipping and rotating devices as in the first section and then transferred to an identical dryer arrangement located above the conveyor guide in the second section. The plates traverse the second dryer and are returned to the conveyor guide where the plates are advanced to an unloading and discharge apparatus. The empty plates are then advanced to the side to side transfer where they are recycled for continued use in the apparatus.

The side to side transfer means includes a pair of plate gripper means each having a movable upper jaw and a movable lower jaw. The upper and lower jaws are each adapted to receive and retain a carrier plate means. A rotation means is attached to each pair of plate gripper means and is adapted to selectively transfer each pair of plate grippers back and forth between the first and second conveyor guides. Each pair of plate gripper means includes means for selectively opening and closing each of the upper and lower jaws. In a preferred embodiment, the opening and closing means includes a cam follower that precisely closes the upper and lower jaws so that carrier plates located in the jaws are positioned in registration with each other in order to clamp product between the plates and to maintain the product clamped in the plates while the gripper means is transferred or rotated between the first and second conveyor guides. In another embodiment, a plurality of engagement pins extend through the carrier plates to engage product in the plates and to transfer the product from a first plate to a second plate. The second plate is aligned in a close proximity to the first plate in the side to side transfer means.

The unloading means includes a means for breaking a seal that may be formed between the coating material applied in the first coating section and the carrier plates during the time in which the second coating is applied to the product. After the seal is broken, the plates are advanced to a discharge means which includes a rotation means for engaging and rotating the carrier plates causing the product to fall to a collection bin. While the plates are in the rotated discharge position, a clean out means which includes a plurality of bars adapted to be extended through the carrier plates is activated to discharge any product that may have adhered to the plate and to remove any excess coating material on the plate.

BRIEF DESCRIPTION OF THE DRAWINGS

FIGS. 7a and 7b are cross-sectional views of another embodiment of a tablet holder of the present invention.

FIG. 8 is a plan view of a product carrier plate of one embodiment of the present invention.

DETAILED DESCRIPTION OF THE PREFERRED EMBODIMENTS

Figure 1:
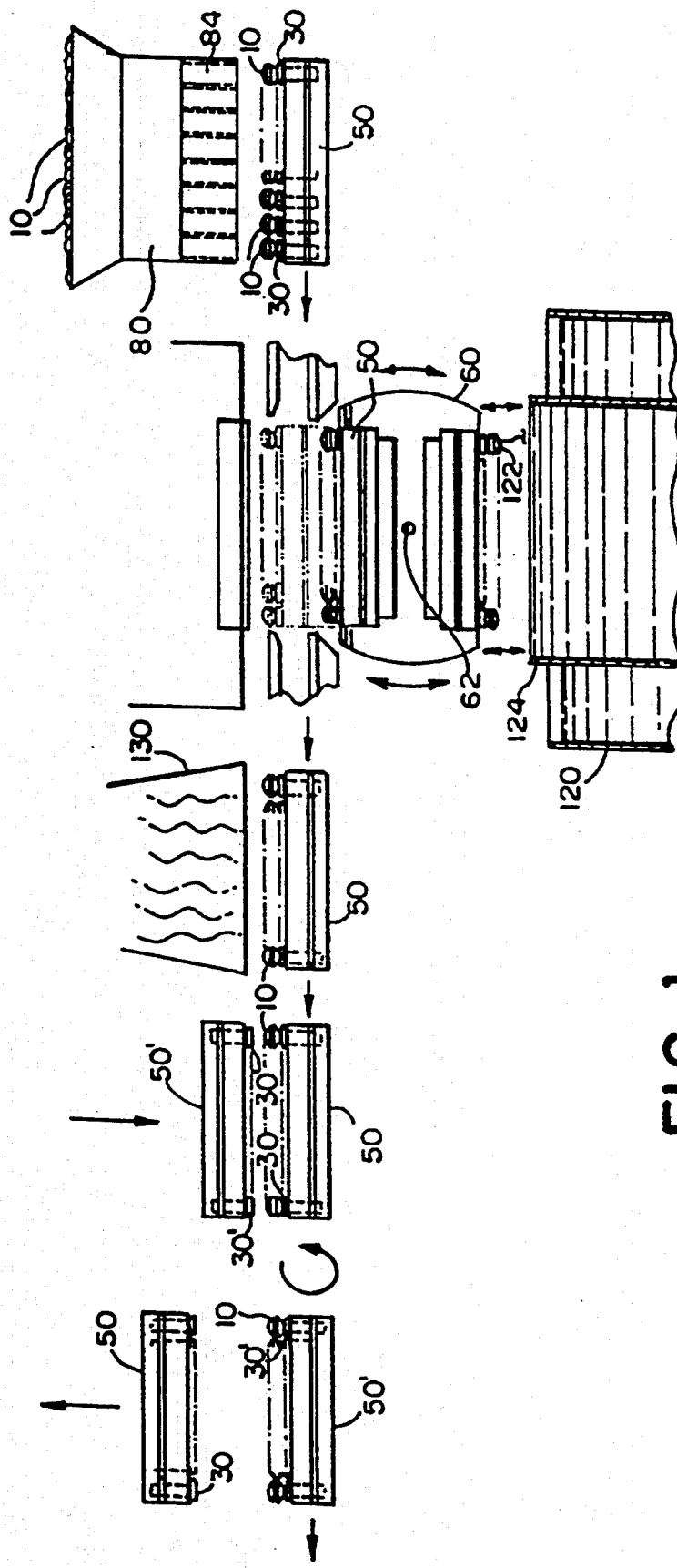
FIG. 1 is a partially diagrammatic, partially schematic representation of the coating apparatus of the present invention.

A generalized representation of the apparatus used in a preferred embodiment of the present invention is shown in FIG. 1. It will be understood that the descriptions set forth may be applied to numerous types and shapes of products. The type of tablet illustrated and the sequence shown are for purposes of explanation only.

A plurality of the product 10 to be coated is placed in a feeder means 80. Preferably, the feeder will be comprised of a hopper 82 and a series of feeder tubes 84 which align, orient and dispense the product 10 in the appropriate manner. Initially disposed directly beneath the feeder tubes 84 and in registration therewith is a plate 50. The plate 50 has a plurality of tablet holders 30 which, as explained below, restrain the product during certain portions of the coating process. The tablet holders 30 preferably correspond to the feeder tubes 84 and thus, most preferably, each tube 84 feeds a single product 10 into a single tablet holder 30.

Conveyor means transfer the plate 50 from the feeder 80 to the vacuum chamber 60. In a preferred embodiment shown in FIG. 1, the vacuum chamber 60 is adapted to receive and make vacuum tight connections with two plates 50. As shown by the arrows, the vacuum chamber 60 is further provided with manipulating means whereby it may be moved up and down, and rotated about a pivot point 62.

A first dipping tank 120 is disposed beneath the vacuum chamber 60 and is filled with a quantity of coating material. Preferably a coating material such as gelatin is used and, most preferably, the dipping tank 120 is provided with pumps and conduits whereby the coating material is continuously circulated. As illustrated, the dipping tank is most preferably constructed to form a meniscus surface 122 by pumping the coating material into an inner tank 124 which is permitted to overflow into the larger tank 120. Such a system prevents the coating material from hardening while the apparatus is in use and helps to ensure that the coating material presents the same even and substantially level surface to the product being dipped at all times.

In operation, the plate 50 is moved into engagement with the vacuum chamber 60 and then the chamber 60 and the plate 50 are rotated one-half revolution. As explained below, the vacuum chamber 60 creates a vacuum within the tablet holders 30 which holds the product 10 in place and in the correct orientation to be dipped. The vacuum chamber 60 is next lowered into dip tank 120 to a predetermined depth and then withdrawn. The vacuum chamber 60 is then rotated one and one-half revolutions in order to return the plate 50 to its original orientation. The additional full revolution beyond that required provides a dwell time, permitting the coating to initially "set" and also prevents the coating from running or sagging due to gravity by constantly reorienting the product 10. However, a rotation of as little as one-half of a revolution may be adequate in some instances. At this point, the plate 50 may be returned to the conveyor means and removed from the vacuum chamber 60.

In an alternative embodiment, a separate rotating station is provided adjacent the dipping station. In this embodiment, the dip station vacuum chamber rotates one-half revolution to return the plate to the conveyor. The plate is then transferred to a second vacuum chamber which engages the plate and rotates one revolution to provide the setting and spreading of the gelatin. The plate is then released and transferred to further processing stations.

The design of the vacuum chamber 60 and placement of the dip tank 120 illustrated permit a wide variety of coatings to be effectively and efficiently achieved. Although the dipping of a substantially cylindrical tablet having concave faces to form a coating having circumferential seam is illustrated, those of ordinary skill will understand that numerous other shapes of product, as well as other coating schemes are possible using the apparatus disclosed. As will be explained below, the shape of the tablet holders 30 and the design of the sub-components of the vacuum chamber 60 may be readily adapted for particular requirements. Also, as illustrated in FIG. 1, throughput may be increased by designing the vacuum chamber 60 to form a vacuum tight seal with further plates 50, such that each time the vacuum chamber 60 is rotated, a plate 50 which has already been lowered into the dipping tank 120 is returned to the conveyor means.

After the plate 50 containing the partially coated product 10 is removed from the vacuum chamber 60 the plate may be passed through a dryer means 130 for curing the coating material. As will be understood by those of ordinary skill, the dryer 130 will be chosen to correspond to the heat and moisture requirements of the coating material being used. Radiant heat, forced hot air, microwave dryers and combinations of these types are among the types available. Depending upon the type of dryer 130 chosen, one or more conveyors and other apparatus may be required to transfer the plates 50 into and out of the dryer 130.

After the coating has been cured, the plate 50 is again returned to conveyor means and is preferably transferred to another location. At this point, although only a portion of each individual product 10 has been coated, it may be desirable to eject the product 10 and consider the process complete. This may be true, for example, where the product has already been coated and the above-described process is carried out to add a second color to a portion of the product.

In a preferred embodiment, however, the present invention provides methods and apparatus which permit the uncoated portion of the product 10 to be coated. First, a second plate 50' is positioned in registration with the product contained on the first plate 50, as illustrated in FIG. 1. The second plate 50' is lowered until the coated side of the product 10 is disposed within the tablet holders 30' of the second plate 50'. The resulting "sandwich" of the first plate 50, the product 10 and the second plate 50' is then rotated one-half revolution by the conveyor/manipulator means. As shown, the positions of the plates 50,50' are thus reversed, and when the first plate 50 is removed the uncoated portion of the product 10 is exposed. The second plate 50' may then be transferred to the starting point of the dipping process and put through the sequence of manipulations necessary to form a coating which were set forth above using either the same apparatus or further apparatus, using either the same coating material or a different coating material.

In the instance where the same apparatus is used to place coating upon the uncoated portion of the product 10, the second plate 50' may be preferably conveyed or otherwise transported to a location just before the vacuum chamber 60, i.e., between the vacuum chamber 60 and the feeder 80 illustrated in FIG. 1. The second plate 50' would simply be inserted into engagement with the vacuum chamber 60 and the above described apparatus would carry out substantially the same sequence of functions in terms of dipping the product 10, curing the coating as needed, etc. After the product 10 has been fully coated and cured, it may be ejected prior to the transfer stage between the first and second plates 50,50'.

In another embodiment of the present invention, after the partially coated product has been transferred to the second plate 50', the plate 50' may enter a duplicate series of apparatus, such as that described above with reference to FIG. 1. In other words, a second vacuum chamber, dipping tank, dryer, and manipulating and conveying apparatus may be provided. After the product 10 is coated and cured using this second set of apparatus, the completed product is ejected.

Figure 2:
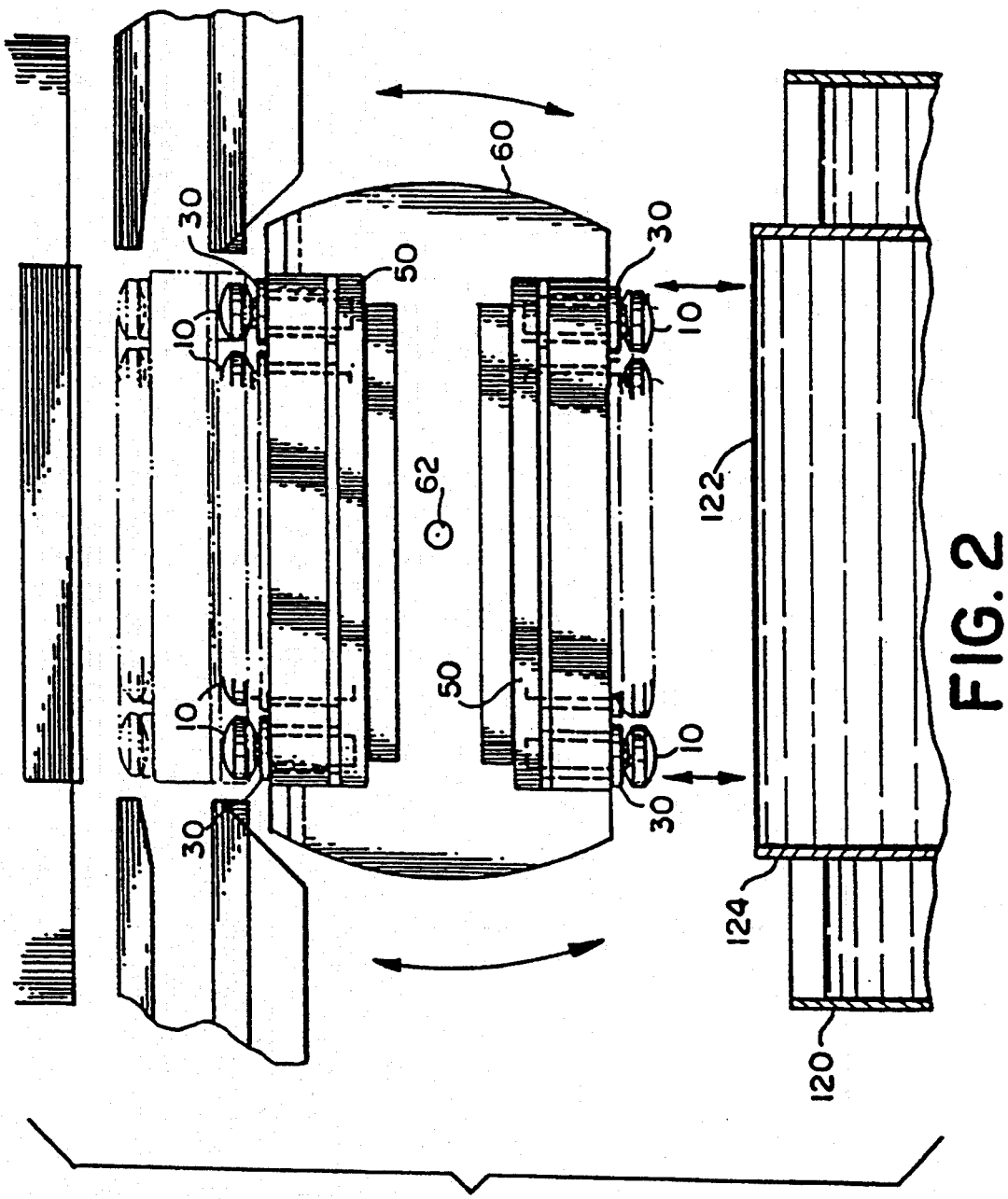
FIG. 2 is a broken away, partially cross-sectioned side view of a portion of the apparatus of FIG. 1.

Referring now to FIG. 2, a more detailed view of the vacuum chamber 60 described above is shown. As explained above, in a preferred embodiment two plates 50 (or 50') are retained in a vacuum tight seal upon the vacuum chamber 60, thereby permitting more efficient indexing between the raising and lowering of the apparatus and the infeed and outfeed of the plates 50 from the vacuum chamber 60.

As shown, the entire chamber may be raised or lowered to bring the product 10 into contact with the surface of the coating material 122. The vertical motion also preferably provides a transfer between the vacuum chamber 60 and the conveyor means, as shown in phantom in FIG. 2. This latter vertical movement also provides clearance when the vacuum chamber 60 is rotated during the dipping process explained above with reference to FIG. 1.

Figure 3:
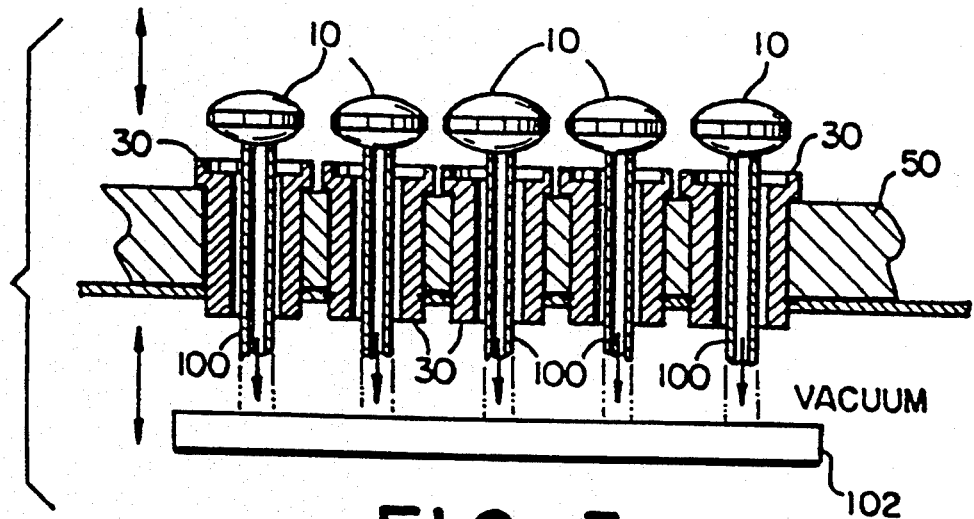
FIG. 3 depicts a cross-sectional view of the tablet holders and plate used in one embodiment of the present invention.

Further details of the vacuum chamber 60 are shown in FIG. 3, which illustrates broken-away section of the plate 50 and the vacuum chamber 60. As seen in cross-section, the plate 50 has a plurality of tablet holders 30 inserted into a series of openings. The plate 50 rests upon the vacuum chamber 60 and forms a seal therewith. A plurality of vacuum tubes 100 extend through the tablet holders 30 and, when in use, engage and slightly lift the product 10 from the tablet holders 30 as shown. The vacuum created within the vacuum chamber 60 is channeled through the vacuum tubes 100 by a manifold or similar means, thereby permitting the vacuum to act upon the surface of the product 10 when contacted by the vacuum tubes 100. By providing vacuum tube actuator means 102 for raising and lowering the vacuum tubes 100 relative to the vacuum chamber 60, the vacuum tubes may be selectively placed in the raised position illustrated. The actuator 102 may be a common bar or mounting structure which is moved by a gear, cam or pulley system.

When in the position illustrated, it is possible to invert or otherwise manipulate the product 10 as described above without friction or the use or mechanically actuated clamps. The vacuum handling system disclosed by the present invention provides a secure retention of the product while minimizing the possibility of damaging either the coating or the product 10 itself. As explained above, the methods and apparatus of the present invention are useful for numerous shapes and sizes of product 10, however, most preferably, the product 10 will have one or more curved surfaces, as illustrated. The curved surfaces permit the tubes 100 to be made from a rigid material such as stainless steel. Those of ordinary skill will realize however, that nearly any shape and any orientation of product may be retained using appropriately designed vacuum tubes. Finally, in certain instances it will be desirable to provide a cushion or resilient tip on the distal end of the vacuum tube in order to ensure a sufficient grip.

Figure 4:
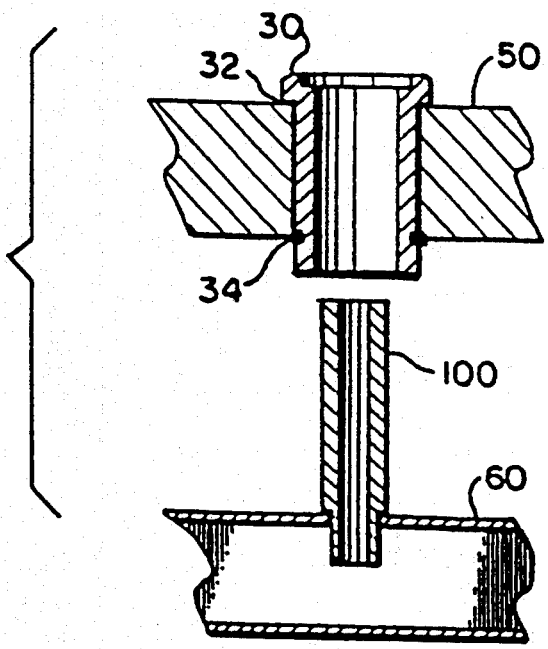
FIG. 4 is a broken away cross-sectional view of the plate of FIG. 3, illustrating the tablet holder and vacuum tube used in one embodiment of the present invention.

Referring now to FIG. 4, one embodiment of the tablet holder 30 is illustrated. A shoulder 32 is formed at a first end of the tablet holder to provide a positive stop. A groove is formed at a second end, into which an "O" ring or the like may be engaged to retain the tablet holder 30 in the plate 50. As will be understood by those of ordinary skill, the tablet holder 30 and the plate 50 may be in certain instances formed as an integral component. FIG. 4 also illustrates the vacuum tube 100 in the withdrawn position. When the vacuum tube 100 is in the withdrawn position, the depression formed in the tablet holder 30 is the only means for restraining the product 10 (not shown in FIG. 4).

FIGS. 7a and 7b show a second embodiment of the tablet holder for use in plates 50. Tablet holder 31 shown in FIGS. 7a and 7b is provided with a plurality of slots 33 forming resilient fingers 35. FIG. 7a is a cross-section taken through the slots 33, and FIG. 7b is a cross-section taken with the holder 31 rotated 90° from its position in FIG. 7a. In the embodiment shown in FIGS. 7a and 7b, a pair of slots 33 are provided thereby forming a pair of resilient fingers 35. Slots 33 are disposed longitudinally through the walls of holder 31. Holder 31 is generally in the form of a cylinder having a central bore 37. Tablet holder 31 is retained in the opening 39 of plate 50 by shoulder portion 41 on one end and angled flange 43 on a second end. For ease in installation the size of upper surface 45 of angled flange 43 may be significantly reduced at the portion of the side walls located immediately adjacent to slots 33 as shown in FIG. 7a. The flange 43 may gradually increase to its largest surface area located 90° from slots 33 as shown in FIG. 7b. The holder 31 is also provided with seat 47 for accepting a tablet therein. It will be understood by those of ordinary skill that the seat 45 may be shaped appropriately to match the shape of the product being held.

The holder 31 is a "push-in" holder that does not require o-rings or the like that are susceptible to wear and tear. In order for the holder 31 to be secured in the plate 50, the outer diameter of the annular resilient fingers 35 forming the cylinder of holder 31 must be slightly larger than the diameter of the opening 39 in plate 50. The angle of flange 43 enables the holder 31 to be inserted through the opening 39 and to cause the fingers 35 to be slightly compressed toward each other as the holder is passed through the plate 50. When the flange 43 clears the opening 39 and plate 50, the resilient fingers 35 spring back to their original position causing flange 43 to engage plate 50 thereby securing the holder 31 therein.

FIG. 8 shows a plan view of a carrier plate 50 for retaining the plurality of product holders 30 or 31. The carrier plate 50 of FIG. 8 includes a plurality of longitudinal rows of individual product holders 31. The plates 50 are preferably from 4 to 5 inches wide and approximately one-half to one inch thick. In one embodiment, the plate 50 is made about 23 to 24 inches in length enabling the plate to include 7 rows each containing 33 holders for a total of 231 holders.

A preferred embodiment of the carrier plate 50 of the present invention is machined from tool plate aluminum. It is also preferred that the aluminum have a protective coating such as an anodized coating applied to the surface. The plate 50 is rectangular and symmetrical, having four easily spaced slots 51 disposed near the four corners which engage the conveyor and/or holding means. Also provided at either end are alignment and transport holes 52 which contain retaining bushings 53 which are used to manipulate the plate 50 as it is advanced through the feeder means 80 and through other processing stations.

The present invention also provides methods for coating a product 10 in accordance with the present invention. A preferred embodiment of the methods of the present invention is illustrated by the sequence of views in FIG. 5. For purposes of illustration and explanation a single product 10, vacuum tube 100 and tablet holder 30 are illustrated, along with broken away portions of other apparatus such as the plate 50. As shown in the upper left section of FIG. 1, a plate 50 containing a tablet holder 30 is positioned beneath the feeder means 80 for feeding a tablet described above and a product 10 is disposed within the tablet holder 30. Next, the plate 50 containing the individual products 10 is moved into the vicinity of the vacuum chamber 60, where it is cleaned of dust and particulate matter. For clarity, the representation of the vacuum chamber 60 is omitted from the other views shown in FIG. 5. An individual vacuum tube 100 is then brought into position and placed in close proximity or contact with the product 10. At this point, the vacuum created within the vacuum tube 100 "picks up" or engages the product 10. After the individual products 10 have been engaged by the vacuum tubes 100, the entire plate 50 is rotated one-half of a revolution, suspending the product 10 by the vacuum tube 100. The vacuum tube 100 and the product 10 attached thereto may now be moved into position and lowered into a coating tank 120. The depth to which the product 10 is lowered is a function of the motion of the vacuum tubes 100 and plate 50, which may be precisely regulated by hydraulic actuators, gear trains or other means for actuating the vacuum tube 100 and/or moving the plate 50. The vacuum tube 100 and the partially coated product 10 are then withdrawn from the coating tank 120, but the product 10 is not fully withdrawn into its holder 30. Instead, the plate 50 and partially extended vacuum tubes 100 are rotated one and one-half revolutions, returning the plate 50 to its initial orientation. Alternatively, the dipping vacuum chamber is rotated one-half revolution and the plate is then transferred to an adjacent second vacuum chamber that rotates the plate one revolution. The additional revolution provides a dwell, permitting the coating to initially set, as well as aiding in the provided evenness of the coating by preventing the coating from running due to gravity. In certain embodiments, however, this dwell may be unnecessary and the plate need only be rotated one-half of a revolution. After the plate 50 has been returned to its initial position, the vacuum tube 100 may be withdrawn until the product 10 again rests in a holder 30 within the plate 50. Once the vacuum tube 100 has been sufficiently withdrawn, the vacuum connection to the product 10 is broken and gravity and the holder 30 restrain the product 10.

Figure 5:
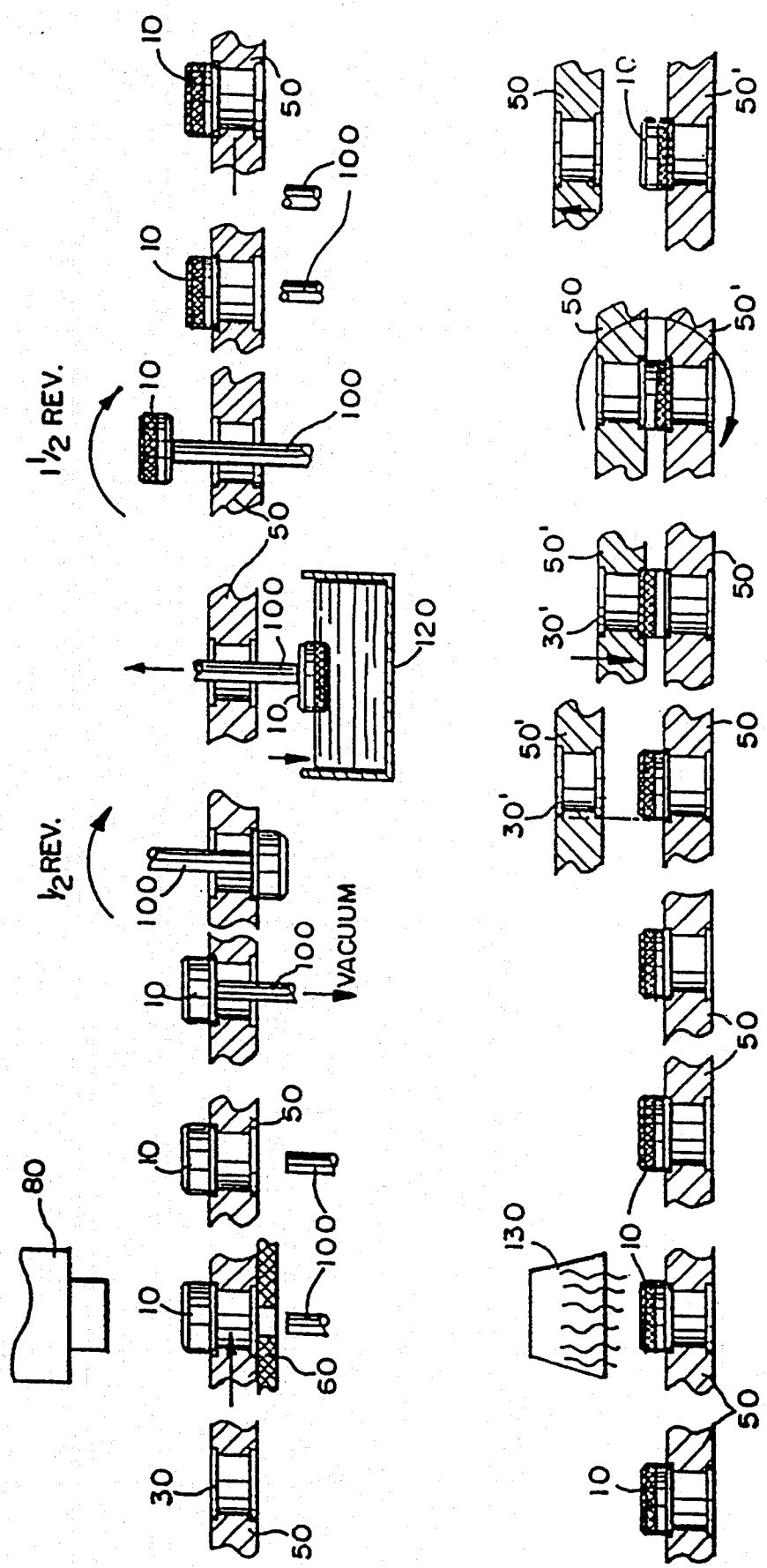
FIG. 5 is a partially diagrammatic, partially schematic representation of the steps of a preferred method for coating a tablet in accordance with the present invention.

As shown at the lower left portion of FIG. 5, once the individual products 10 have been released from the effect of the vacuum, the plate 50 bearing the partially coated individual products 10 may be moved into a dryer 130. Using conveyors or other conventional means, the plates are pushed into the dryer 130 and dried. After the coating has cured and the plates 50 have exited the dryer 130, a second plate 50' is moved into position such that the tablet holders 30' in the second plate 50' are in registry with the tablet holders 30 in the first plate 50, which contain the partially coated product 10. The second plate 50' is lowered toward the first plate 50 until the tablet holders 30' in the second plate 50' have engaged the product held in the first plate 50. Thus, as illustrated, the product 10 is "sandwiched" between the first and second plates 50,50". The pair of plates 50,50' are then rotated one-half revolution, thereby reversing the relative positions of the first and second plates 50,50'. The first plate 50 is then raised, leaving the uncoated portion of the product 10 on the top, exposed, and the coated side on the bottom, i.e., within the tablet holder 30 of the plate 50'.

At this point, the preferred embodiment of the method illustrated has completely coated and cured a coating on about one-half of the product 10. It will be understood, however, that the above-described method may be repeated by transferring the plate 50' shown in the lower right section of the illustration to the upper left section, in other words, to the beginning of the process at the point immediately after the individual products 10 have been loaded into the plates 50. In this embodiment of the present invention, the above-described process is repeated and the remainder of the product 10 is coated. It should be further understood, however, that in any event, more or less than one-half of the tablet may be coated to provide different overall coating effects. For instance, if both "passes" coated less than one-half the height of the tablet, a band of uncoated product would remain exposed. On the other hand, if one or both of the "passes" were carried out to a depth substantially greater than one-half the height of the tablet, an overlapped "seam" appearance would be created.

Figure 6:
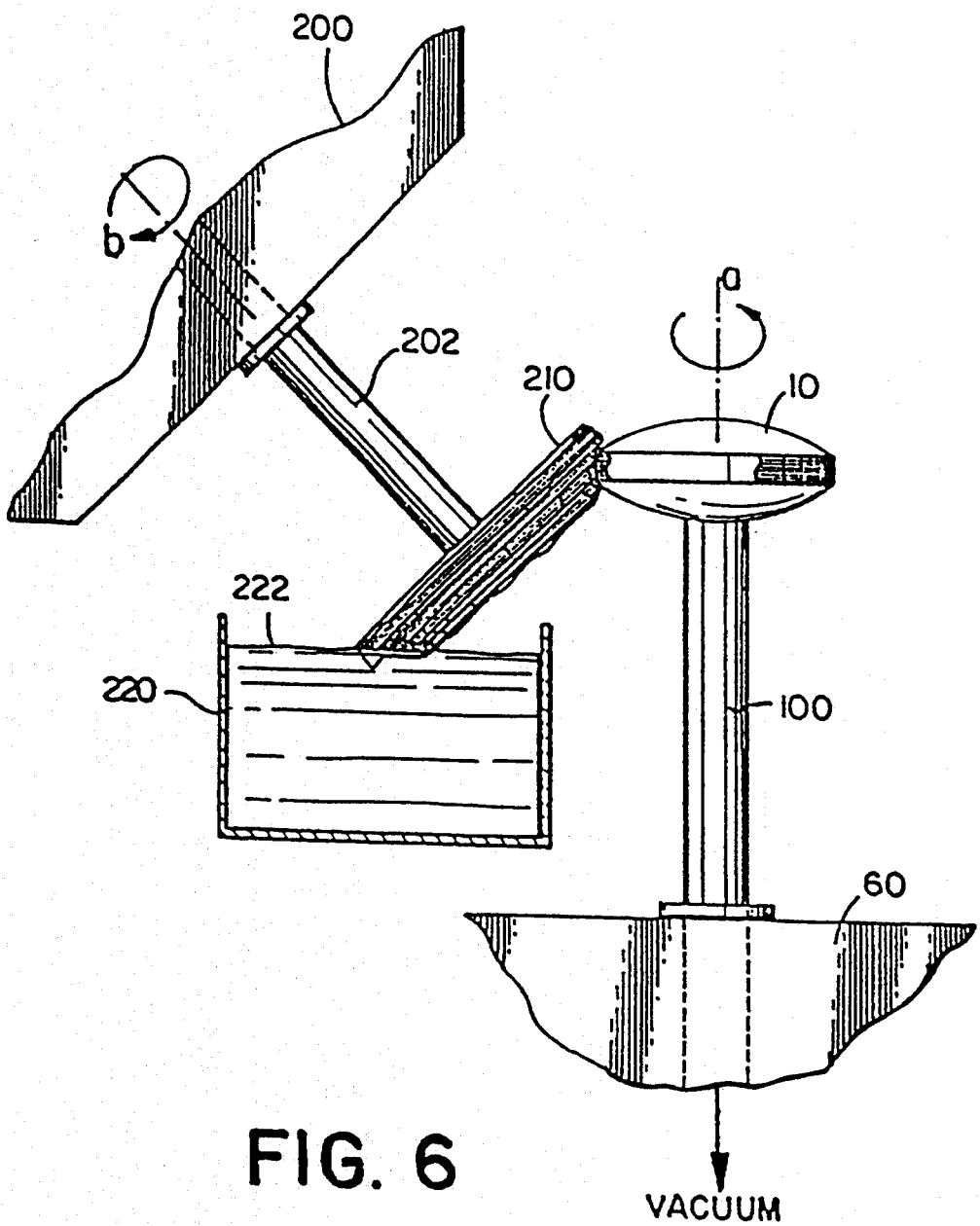
FIG. 6 is a broken away cross-sectional view of a portion of another embodiment of tile present invention in which a band of coating material is applied to the products.

Referring now to FIG. 6, another feature of certain embodiments of the present invention is illustrated. In these embodiments, the vacuum tube 100 will be constructed such that it may be rotated about its longitudinal axis as shown by arrow a in FIG. 6. As understood by those of ordinary skill, such rotation may be accomplished using gear trains, belts and pulleys or other means for transferring rotational motion to a shaft. While rotating, the vacuum tube 100 is also acted upon by a source of vacuum, either the vacuum chamber 60 discussed above, or another source. The product 10 is thus firmly held in place upon the rotating vacuum tube 100 as shown. While the product 10 is rotating, it is brought into contact with a rotating wheel 210 or other application means for applying a coating. Preferably, the rotating wheel 210 provided is shaped and manipulated so as to come into close proximity with a portion of the product 10, such as the central "edge" shown. As the wheel 210 and product 10 rotate, the wheel 210 also passes through a quantity of coating material 222 and precisely coats a portion of the product 10. The wheel 210 rotates about a shaft 202 in the direction shown by arrow b and is mounted on a support structure 200 at an appropriate angle.

The present invention therefore also discloses methods whereby a relatively narrow stripe or band of coating material may be applied to a product. Most preferably, the product and the means for applying the coating rotate and are placed in close proximity. The means for applying the coating is preferably at least partially immersed in a quantity of coating material and passes therethrough while rotating. Using the embodiments illustrated in FIG. 6, it is possible not only to provide a different color "band" or stripe, but to also increase the thickness of the coating in a specified section, thereby creating the appearance of a seam or an overlapped gelatin capsule.

Figure 9:
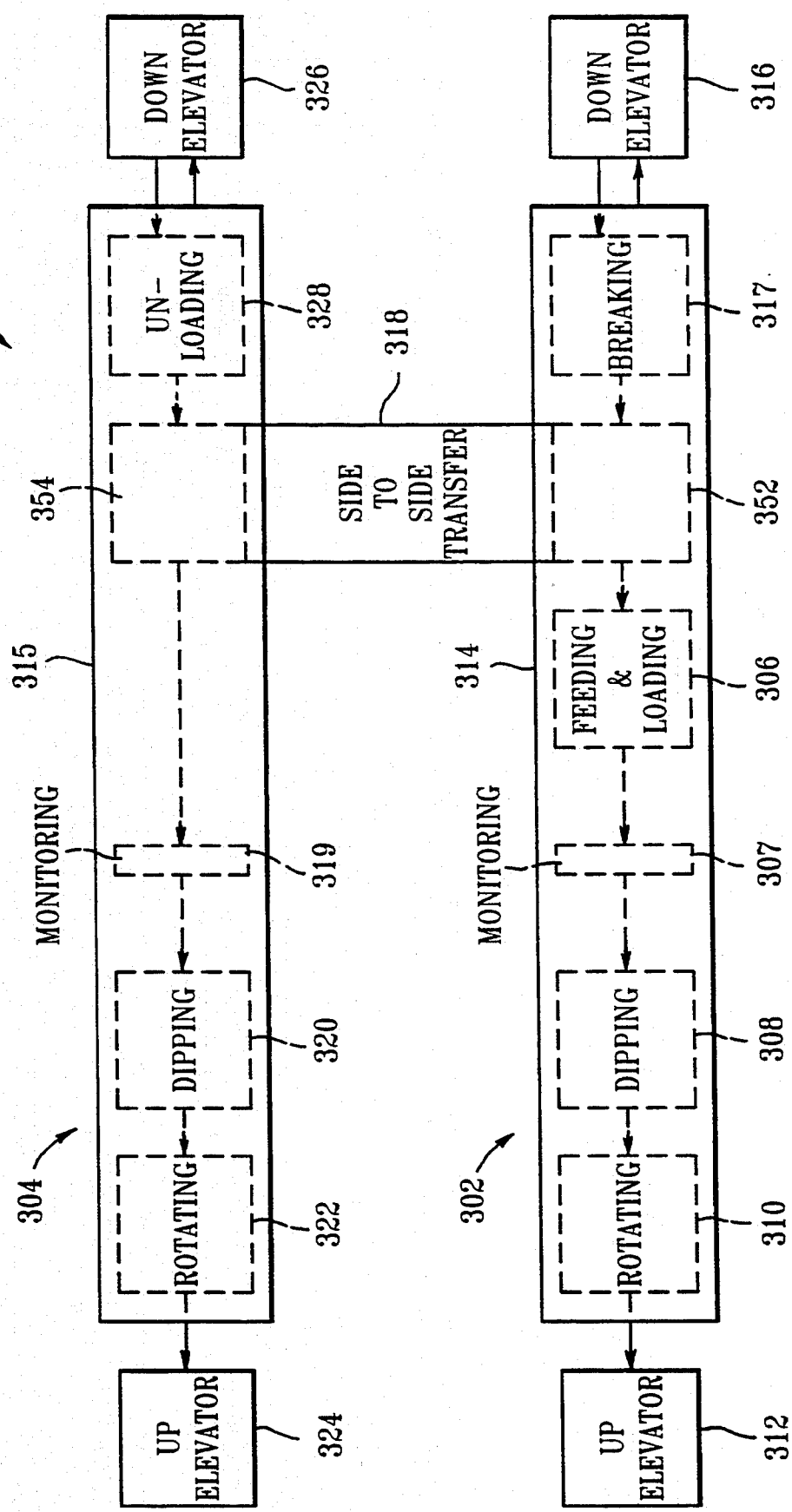
FIG. 9 is a block diagram of the arrangement of the processing stations of a duplex coating apparatus of the present invention.

As stated above, in one embodiment of the present invention, a duplex coating apparatus is used for applying two or more coatings to the product. FIG. 9 is a block diagram showing in a top view the general arrangement of the various processing stations of a duplex coating apparatus 300. The apparatus 300 includes a first coating section 302 and a second coating section 304. The plate are advanced in each section 302 and 304 along a conveyor to the various processing stations. The first coating section 302 includes a feeding and loading station 306 where products are fed from a storage container to a loading apparatus for loading products onto the carrier plates. A detailed description of a feeding and loading apparatus that may be used in connection with the present invention is disclosed and described in my related patent application, Ser. No. 08/003,334, which is commonly assigned and which is hereby incorporated by a reference as if fully set forth herein.

Figure 9A:
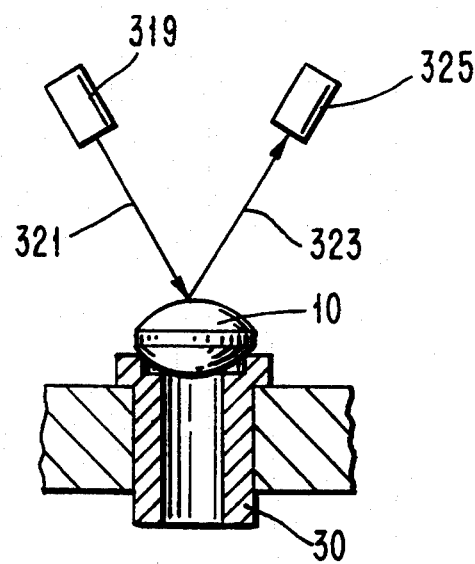
FIG. 9(a) is a broken away, partial cross-sectional view of the light reflection system used in the monitoring station of the present invention.

After the tablets leave the feeding and loading station 306, the plates pass through a monitoring station 307. The monitoring station 307 detects the presence of unfilled tablet holders. In addition, the monitoring station 307 detects the presence of broken tablets in holders. As is conventional in this art, the coating apparatus is controlled by a computer control system. It is typical in these systems to have the capability to track the location of each of the plates as they travel through the apparatus. Upon a plate being detected with either missing tablets or broken tablets, the control system will be signalled and the information stored in the system. The control system is adapted such that when an identified plate reaches either of the dipping stations, the plates will not be dipped. Plates having empty holders, if dipped, will result in gelatin being sucked into the vacuum system through the vacuum tubes which will be avoided by the present invention. In addition, tablets may be broken to the point where they cannot be held by the vacuum tubes and the broken tablets will fall into the gelatin, or the broken tablets will leave an open space allowing gelatin to be sucked into the system. The plates so identified are otherwise treated the same but will not be emptied into the collection bin as will be described later in connection with the unloading station. The monitoring station may utilize a light reflection system as generally shown in FIG. 9(a). A tablet 10 is shown positioned in a holder 30. At the monitoring station 307, a light source 319 directs a light beam at the center of holder 30. If a tablet is in the holder, a light beam 323 will reflect from the tablet and be sensed by detector 325. If no tablet is in holder 30, the light will not be reflected back to the detector but will pass through the holder 30. The detector is connected to the computer control system and if a detector fails to sense the presence of a tablet in the holder, the computer will identify the plate as containing an empty holder. A more complex but well known light detection system may be used in which the detector will be programmed to sense a particular light pattern representative of a full unbroken tablet. The detection of a light pattern that deviates by a certain degree will indicate a broken or defective tablet and the computer system will register that plate as containing scrap product.

The first section 302 also includes a dipping station 308 and a rotating station 310. As described previously, at the dipping station 308, a first portion of the product is coated. The plates containing the partially coated product are advanced to the rotating station where the plates are rotated at least one revolution for spreading the coating evenly throughout the first portion of the product. The vacuum chamber systems as described above may be utilized at the dipping and rotating stations. Additionally details of these systems can be found in another of my related U.S. patent applications, Ser. No. 08/003,158, which is also commonly assigned and which is also hereby incorporated by reference as if fully set forth herein.

Figure 10:
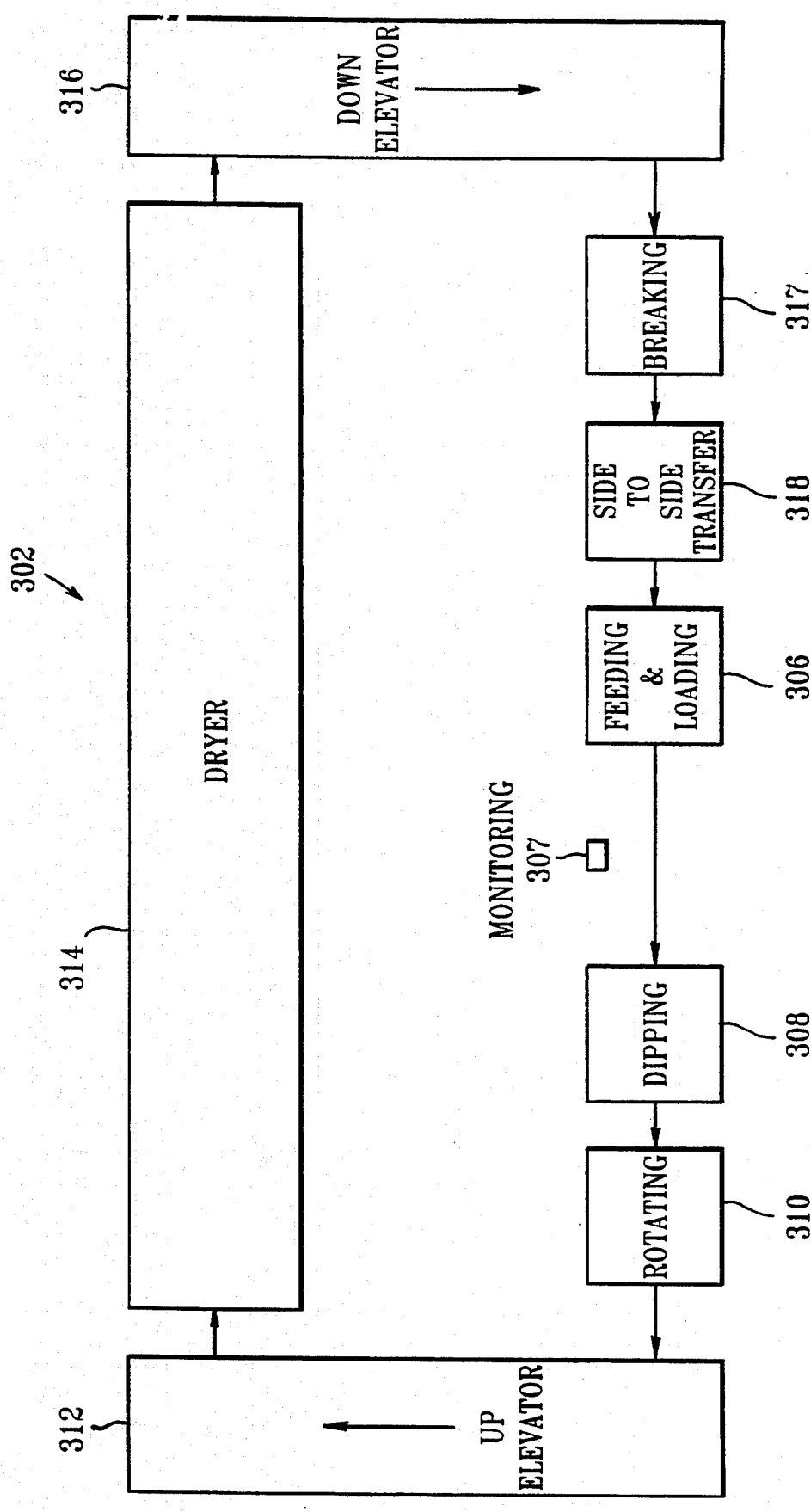
FIG. 10 is a block diagram of one section of the duplex coating apparatus of FIG. 9.

After the dipping and rotating stations, the carrier plates are transferred to a dryer for curing the coating on the first portion of the product. In order to make the most economical use of manufacturing facilities and space, the preferred embodiment of duplex coating apparatus 300 includes dryer means 314, 315 positioned above the first and second coating sections 302, 304, respectively. As shown in FIG. 10, section 302 includes dryer 314 positioned between an up elevator 312 and a down elevator 316. In order to transfer the carrier plates to the dryer up elevator 312 receives plates from rotating station 310 and raises the plates up to the dryer 314. The carrier plates containing the partially coated product are transferred from the up elevator 312 into the dryer 314 where they are transported through the dryer and into the down elevator 316. Down elevator 316 returns the carrier plates to the conveyor in the first section 302 where they are advanced to a side to side transfer 318. The side to side transfer 318 transfers the partially coated product to the second coating section 304 such that the product is positioned on the carrier plates with an uncoated second portion being exposed.

During the coating process in the first coating section 302, gelatin may drip over the entire product and contact the holder. The gelatin will become dried and possibly form a seal between the tablet and holder that may prevent the tablet from being transferred to the plate in the second coating section, i.e. the table adheres to the plate. At the breaking station, pins are inserted through the holders in a controlled manner to lift the tablets off the holder seats thereby breaking any such seals that may have formed. The tablets are carefully returned to the holders and the plates are advanced to the side to side transfer 318. A more detailed description of the breaking station may be found in the description for FIG. 15.

The carrier plates in the second section 304 first pass under monitoring station 319 then advance to dipping station 320 where the exposed portion of the product is coated. As in the first section however, if missing or broken tablets are detected at the monitoring station, these plates will not be dipped. The plates are thereafter advanced to rotating station 322 for spreading the coating on the second portion of the product. The plates are then advanced to an up elevator 324 for transfer to dryer 315. The plates are transported through the second dryer 315 to down elevator 326 which returns the plates to the conveyor. The plates are then advanced to an unloading station 328 where the fully coated product is ejected and collected. Empty plates are then advanced to the side to side transfer 318 for transfer back into the apparatus for reuse.

The plates that are returned to the conveyor in the first section 302 advance to the side to side transfer 318 to transfer the product to section 304 in order to allow for coating of a second portion, for example, the second half of the product. The side to side transfer 318 operates to continually recycle the product carrier plates thereby providing an efficient high production system. To expose the uncoated portion of the product an identical empty product carrier plate is placed on top of the plate having the partially coated product in section 352 of side to side transfer 318. Section 354 at this timing point has two empty product carrier plates positioned facing each other. The side to side transfer 318 is then rotated 180° in order to shift section 352 to section 304 and to shift section 354 to section 302. The product is then shifted by gravity onto the empty plate in section 352 and is advanced through the dipping station 320, rotating station 322 and into up elevator 324 for transfer to dryer 315. A fresh empty plate from section 354 is then advanced to the feeding and loading section 306 for reloading and dipping of newly loaded product. The side to side transfer 318 continues to rotate 180° to shift the plates in this manner to provide the continuous recycling of the plates.

Figure 11:
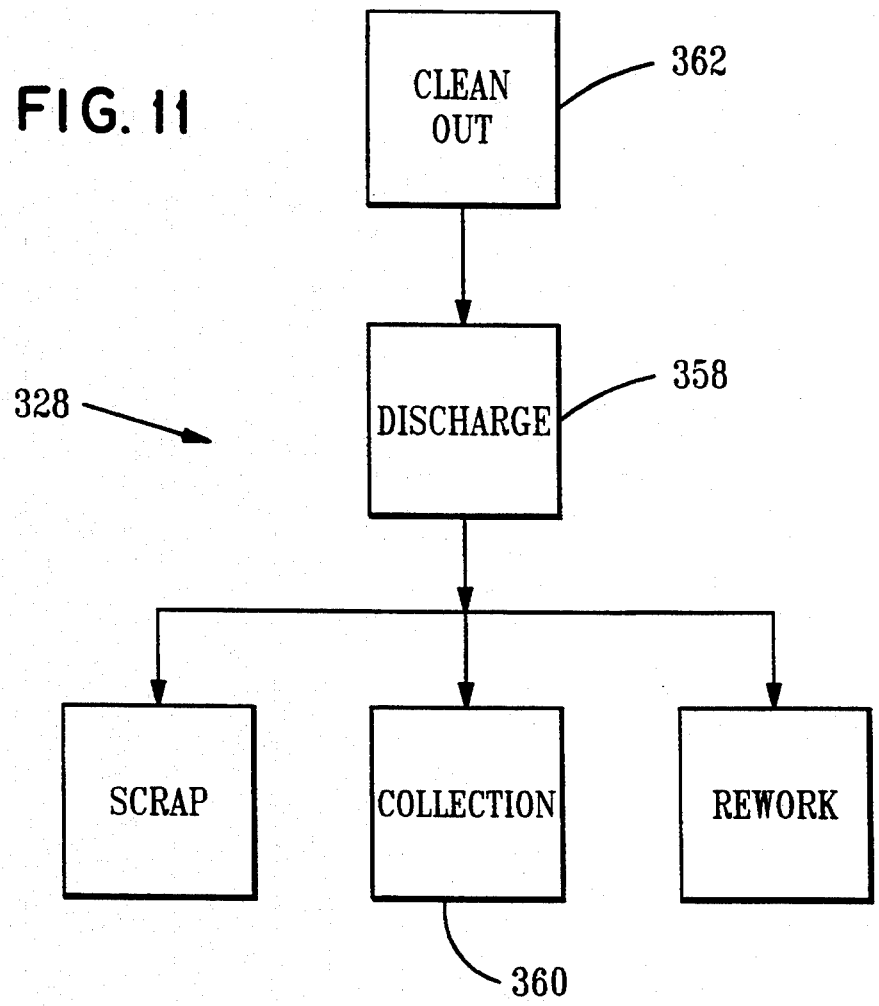
FIG. 11 is a block diagram of the unloading stations of the apparatus of FIG. 9.

After the plates traverse dryer 315 to cure the coating on the second portion of the product, the plates are shifted by down elevator 326 to the conveyor and advance to the unloading station 328. FIG. 11 is a block diagram showing the various components of the unloading station 328. The plates are advanced to the discharge unit 358 where the plates are rotated 180° so that the products are removed from the plates by gravity into the collection bin 360. While the plates are in the rotated position a clean-out means, such as a reciprocating pin mechanism is actuated to extend pins through the holders to break any seals between the tablets and holders formed by the coating applied in the second coating section to ensure all tablets are discharged. The tablets are initially received onto a movable conveyor that includes a divider means for directing the tablets into different collection bins. The divider means is automatically activated to convey the tablets into a finished product collection bin, a rework bin or a scrap bin, depending on whether the plates have been identified by the monitoring stations as containing missing or broken tablets. Tablets in plates containing only missing tablets will be conveyed to the rework bin to be reused in the apparatus. Plates with broken tablets will be conveyed to the scrap bin. All other tablets will be conveyed to the finished product bin. The cleaned out plates are then advanced to the side to side transfer 318 to be reused in the continuous operation of the coating apparatus.

Figure 12:
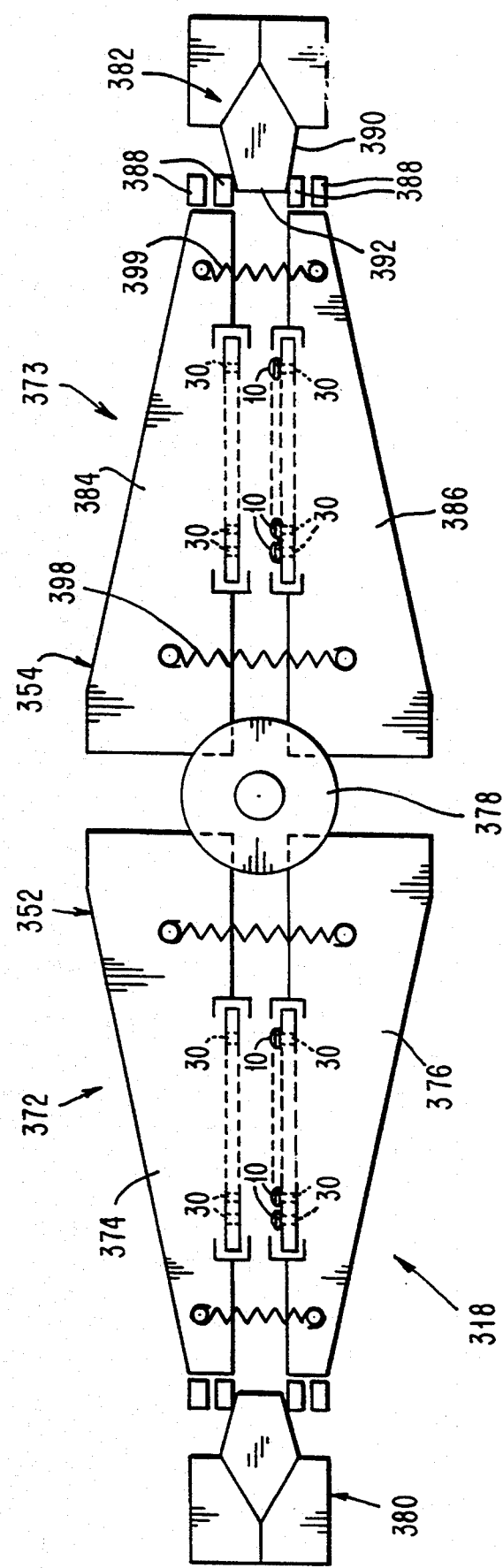
FIG. 12 is a diagrammatic view of the side to side transfer means of the present invention.

Referring now to FIG. 12, a schematic diagram of the side to side transfer 318 is shown in an end view of the duplex apparatus so that both section 352 and section 354 can be seen. Side to side transfer 318 is comprised of a pair of plate gripper means 372 and 373. The plate gripper means 372 includes a movable upper jaw 374 and a movable lower jaw 376 and plate gripper means 373 includes movable upper jaw 384 and movable lower jaw 386. Each of the jaws 374, 376,384 and 386 are adapted to retain a carrier plate 50. The transfer means 318 includes a rotation means 378 attached to each pair of plate gripper means 372 and 373. The rotation means 378 is adapted to selectively transfer each pair of plate gripper means back and forth between the first and second conveyor guides in the coating sections.

Figure 13:
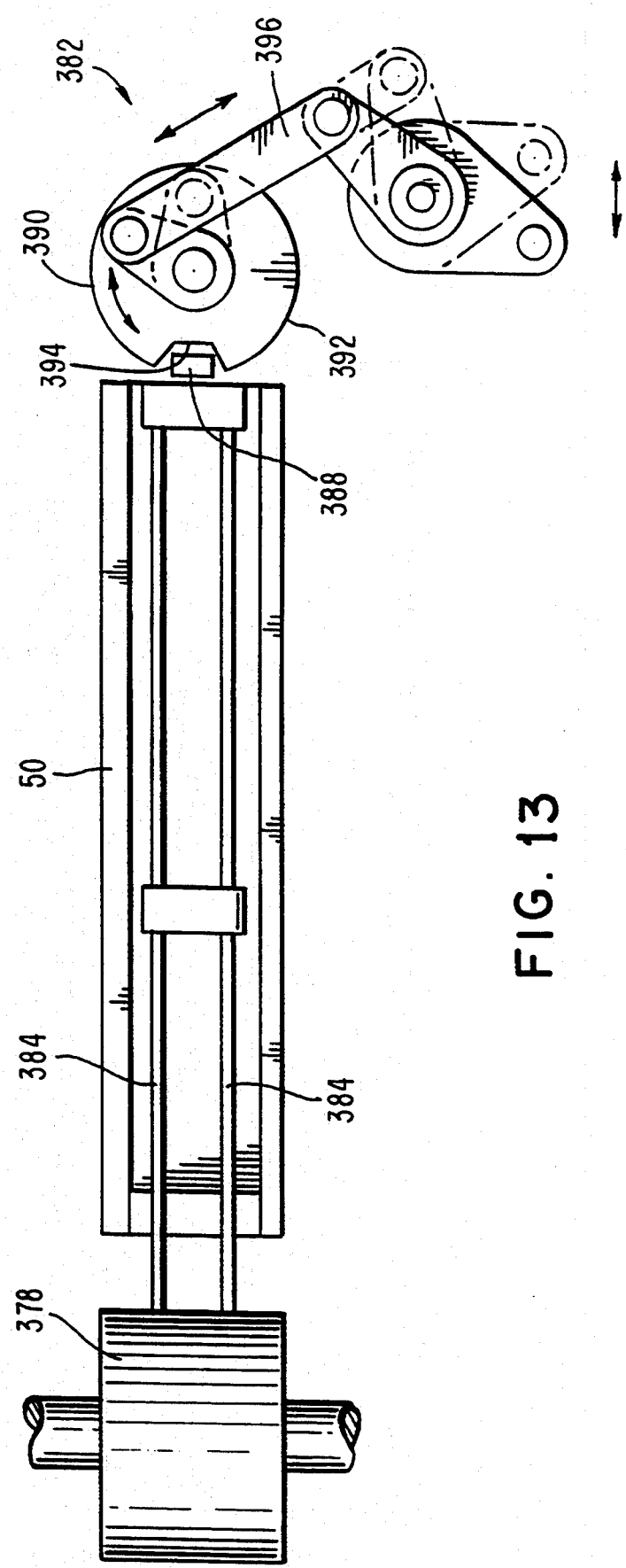
FIG. 13 is a partial diagrammatic top view of the side to side transfer means of the present invention.

Each pair of gripper means 372, 373 includes means for selectively opening and closing the upper and lower jaws. Gripper means 372 includes a cam follower means 380 for opening and closing jaws 374 and 376. Gripper means 373 includes cam follower means 382 for opening and closing jaws 384 and 386. Cam follower means 382 includes double cam 388 attached to gripper 384 and 386. Cam follower 390 as better shown in FIG. 13 is a generally circular cam having a wide portion 392 and notched portion or opening 394. The width of the cam gradually increases from the notch to the wide portion 392. A linkage mechanism 396 reciprocates the cam 390 between the position shown in FIG. 13 in which the notch is aligned with the cam follower 388 and the position shown in FIG. 12 in which the wide portion 392 is between the cam followers 388. Springs 398 and 399 bias the grippers 384 and 386 together. When cam followers 388 are separated by cam 390, the grippers separate allowing the plates 50 to be transferred onto the conveyors and to allow new plates to be transferred into the grippers. When the cam rotates back, the spring biasing closes the grippers so that the plates 50 in each gripper are in registration.

Referring back to FIG. 12, jaws 374, 376 each retain a carrier plate means 50 such that product holders 30 in each of the plates are in registration, i.e. the holders are aligned vertically one above the other. Upon actuation of the cam follower means 380, jaws 374 and 376 move towards each other until the product 10 located in the holders of jaw 376 are sandwiched between the holders of the two plates 50. The cam follower means 380 retains the plates in a closed position such that the product is clamped between the holders. The product remains clamped therebetween while the gripper means 372 and 373 are rotated 180° to transfer the plates to the opposite conveyor guide. Once rotated, jaw 374 will then become the lower jaw and 376 will become the upper jaw. The cam follower means 380 is actuated to open the jaws. Upon opening, the product 10 will then be retained in the holders 30 of the plate located in jaw 374, which plate is now in the conveyor guide of the second coating section. This plate 50 is then advanced to the processing stations for coating the second portion of the product. At the same time that the plate in jaw 374 is advanced into the second conveyor guide, an empty plate that has just be unloaded at station 328 is transferred into jaw 374. Again, this happens while jaw 374 is located in the lower position while section 352 is aligned with second conveyor guide 315. Also, during that same timing period, an empty plate located in jaw 384 is advanced to feeding and loading station 306 and a fresh plate having partially coated product is advanced into jaw 384. An empty plate is located in jaw 386 ready for the product in jaw 384 to be transferred thereto. The side to side transfer 318 is then rotated 180° again so that jaws 374 and 376 are again located and positioned on conveyor guide 314. The plate in jaw 376 from which product has just been transferred from is now empty and is advanced to feeding and loading means 306 and a new plate is transferred into jaw 376 having a coated product on one portion. Thus, from the above description it can be understood that the plates that are advanced in section 302 are continually recycled within section 302 and the plates that are advanced in section 304 are continually recycled for reuse in section 304.

Figure 14:
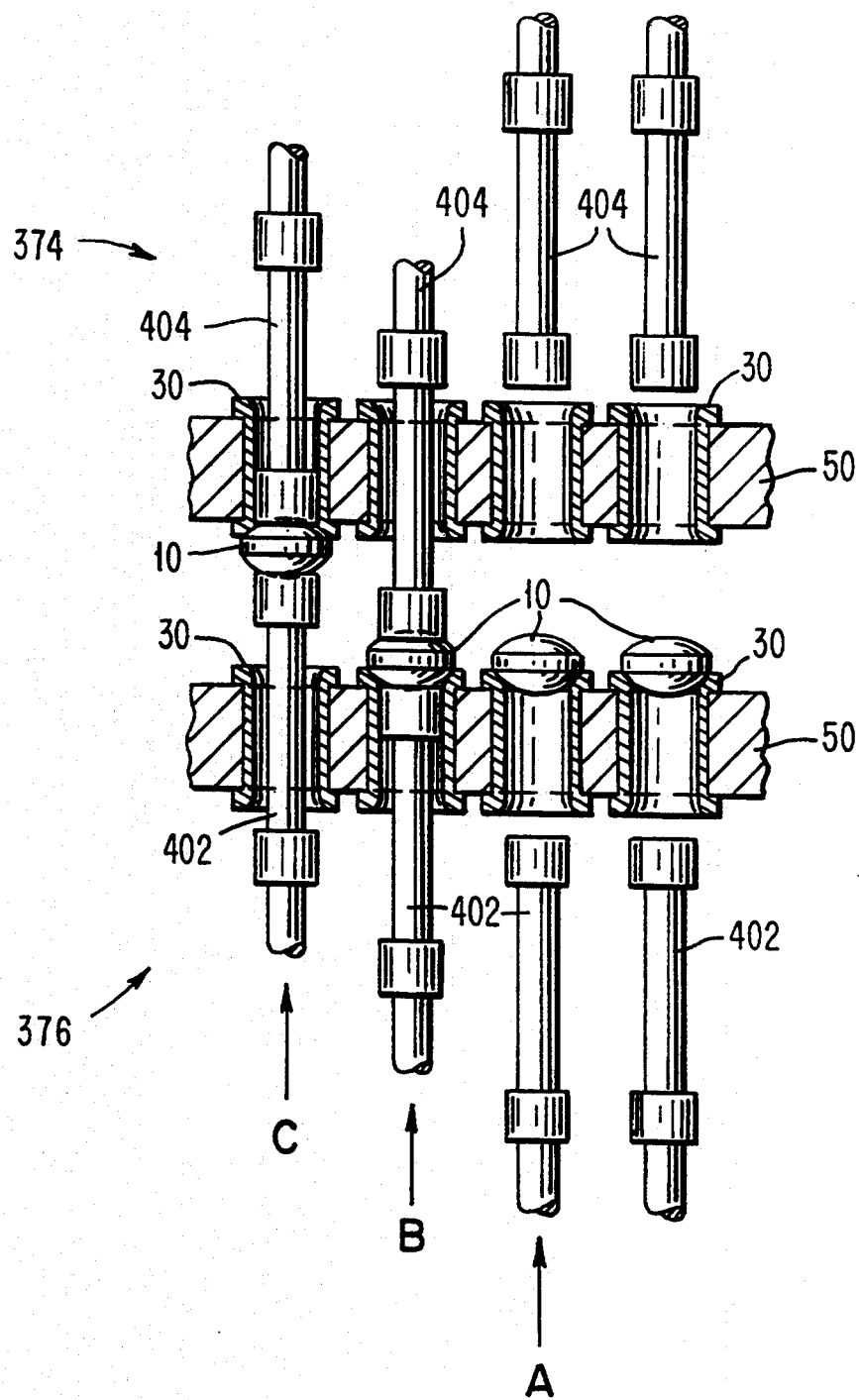
FIG. 14 is a diagrammatic view of an alternative embodiment of the side to side transfer means of the present invention.

An alternative embodiment for transferring product from jaw 376 to 374 is diagrammatically shown in FIG. 14. In this embodiment, jaw 376 includes a plurality of engagement pins 402 and jaw 374 includes a plurality of engagement pins 404. The engagement pins 402 and 404 are adapted to be extendable through product holders 30 in the carrier plates 50 held in the respective jaw. FIG. 14 shows how the transfer is effected in sequence. In position A, bins 402 and 404 are fully retracted from the respective plates 50. In position B, the pins 402 and 404 are extended through the respective holders of the plates 50 to sandwich the product 10 while the product is still retained in holders in jaw 376. In position C, pin 402 is extended while pin 404 is retracted to maintain the product 10 sandwiched between the pins and thereby shifting the product from the holders in jaw 376 to the holders in jaw 374. With the pins held in position C, the transfer means 318 is rotated 180°. The pins are then retracted from the plates to allow the plate to be advanced for processing.

Figure 15:
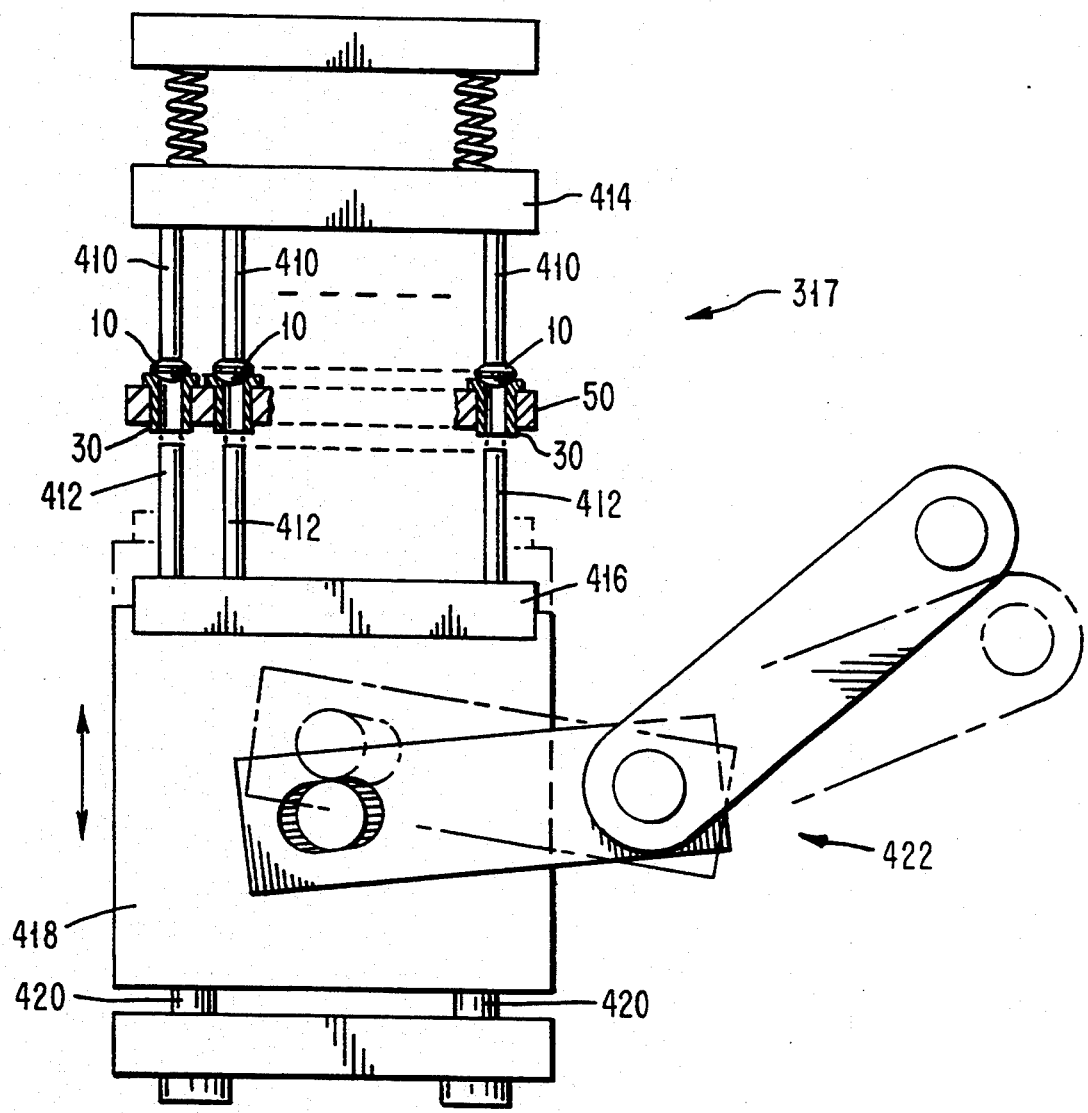
FIG. 15 is a diagrammatic view of the seal breaking means of the present invention.

Referring now to FIG. 15, there is shown a detail of the breaking station 317. The breaking means 317 breaks a seal formed between the coating material that has been applied to the product by the first coating means. The breaking means 317 includes a plurality of pairs of engagement pins 410 and 412. The pins 412 are extendable through product holders in a plate 50 that is positioned in the breaker station. The pins extend through the holders and come in contact with the product 10 to lift the product 10 off the holders by a small distance. The pins 410 are attached to a mounting bar 414 that is spring biased so that the pins 410 are in a close spaced relation with the product while the product rests in the holder 30. When the pins 412 extend through the holder and lift the product 10 off the holder, the product then comes in contact with the pin 410 such that the pins 410 and 412 sandwich the product while it is lifted off the holder. The lifting of the product off the holder will break any seals that may be present between the coating material that has been applied to the first portion of the product during the time when the product is being processed through the first coating means. The breaking of the seal facilitates transfer of the products to the second coating section. Upon the retraction of the pins 412 out of the holders 30, the spring biasing of pin 410 returns the product to the holder 30. The pins 412 are secured to a mounting bar 416. Mounting bar 416 is secured to block 418 that is movable in a vertical direction along rods 420. A linkage mechanism 422 actuates to move the block 418 from the fully retracted position shown in FIG. 15 to the fully extended position in which the pins 412 cause the product 10 to be lifted off the holder 30. Linkage means 422 is a cam operated linkage means adapted to extend and retract the pins 412 through the holders 30 upon a plate 50 being advanced from the down elevator 326 into the breaker station 356.

Figure 16:
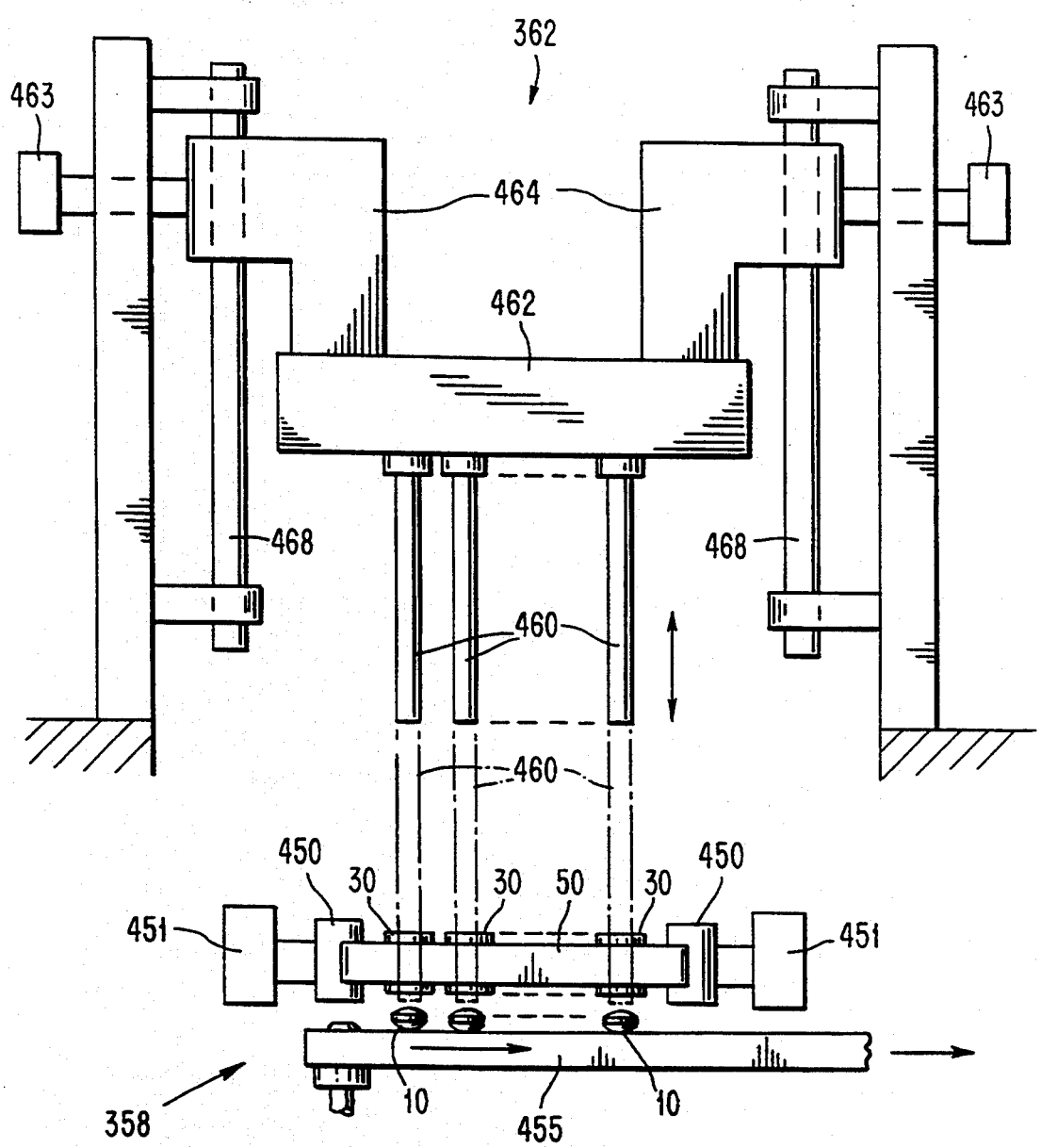
FIG. 16 is a diagrammatic view of the unloading means of the present invention.

After the plates are advanced through the dipping, rotating and drying stations in the second coating section, the plates are advanced to the discharge and clean out means 358, 362. In a preferred embodiment of the unload and clean out stations, both of these functions are performed while a plate is located in the same physical location in the apparatus. The plate 50 having product coated on both sides is engaged and rotated 180° in order to cause the tablets to fall by gravity into a collection bin. While the plate is upside down, any seals that may have formed during processing in the second section are broken and products are cleaned out of the plates by extending a plurality of clean out pins through the holders. The pins are retracted and the plate is then returned to its upright position and advanced to the side to side transfer means where it is ready to be reloaded with product from the first coating section. FIG. 16 shows the discharge station 358 having a plate 50 being engaged by rotatable engagement means 450 that is driven by a cam operated linkage means 451. As shown in FIG. 16, the plate 50 has been rotated and product 10 has dropped onto a conveyor 455 which carries the product to the collection bins. As noted above, the product from each plate is directed into a finished product bin, a rework bin or a scrap bin. Any suitable means may be used to selectively change the point at which product drops off the conveyor thereby directing the product into the desired bin.

FIG. 16 also shows the clean out station 362 which includes a plurality of clean out bars 460 attached to mounting bar 462 that is driven by cam operated linkage means 463. Sliders 464 are attached to mounting bar 462. The sliders slide along shafts 468 to move the clean out bars 460 from the fully retracted position shown, to the fully extended position shown in phantom, in which the pins extend through a plate 50 that has been rotated upside down.

Figure 17:
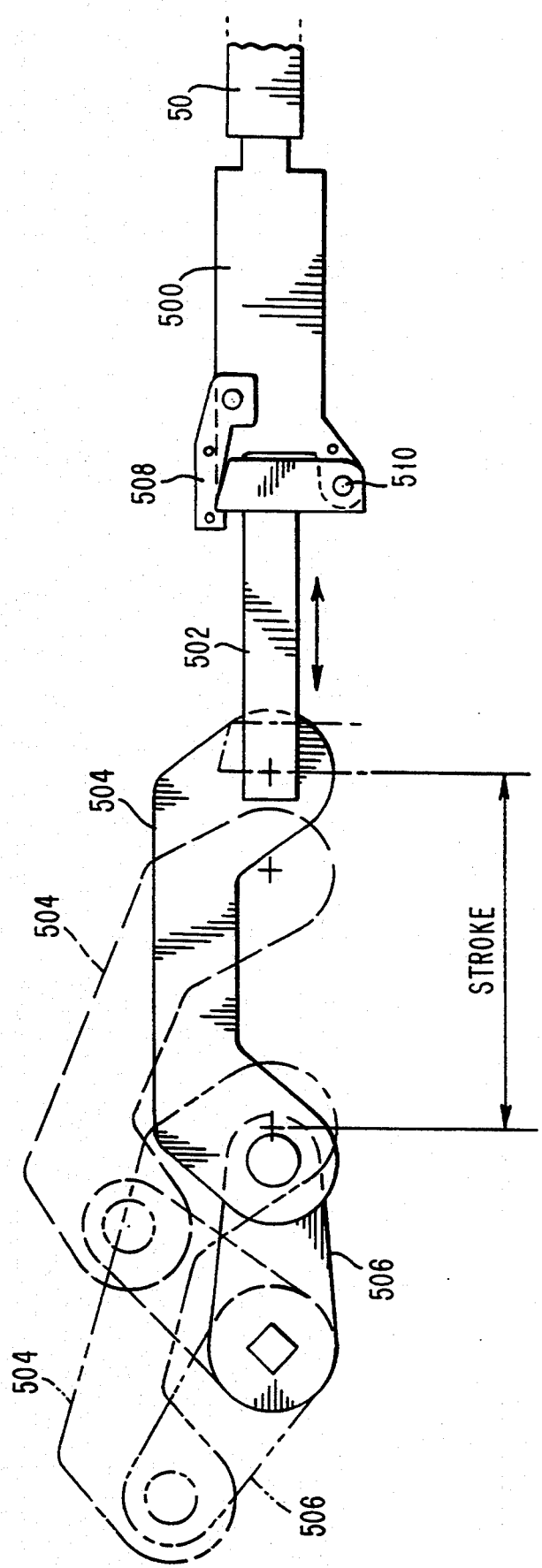
FIG. 17 is a diagrammatic view of one carrier plate advancement means of the present invention.

Also included in both the first and second coating section is means for advancing the plates on the conveyor guide after the plates are returned from the down elevators. FIG. 17 shows one embodiment of this advancement means. Plate 50 is pushed by a releasable extension bar 500. The bar 500 is releasably attached to pusher bar 502. Bar 502 is attached to the second of a pair of pivoting pusher bars 504 and 506. Bars 504 and 506 are shown in solid lines in the retracted position for receiving plates from the elevator. Bar 506 is rotated to the position shown by a dash-dot line. Bar 504 is caused to move from the retracted position to the fully extended position also shown by the dash-dot line. Intermediate positions of these bars are shown by dash lines. The full stroke produced by the movement of bar 504 advances the plates to the breaking station or the unloading station. The bar 500 is releasable by releasing lever 508 which allows bar 500 to be moved a small distance away from the plate 50 and then pivot at point 510. In the event of a system shut down plates will be effectively locked one against the other because of the nature of the advancement of mechanically moving plates against each other. The release of bar 500 allows plates to be removed if need be during a shut down.

While the invention has been particularly shown and described with respect to the preferred embodiments thereof, it should be understood by those skilled in the art that the foregoing and other changes in form and detail may be made therein without departing from the spirit and scope of the invention which should be limited only by the scope of the appended claims.

What is claimed is:

1. An apparatus for coating a product comprising:
   a first plurality of carrier plate means for receiving and retaining a plurality of product;
   means for loading a plurality of uncoated products onto said first plurality of carrier plate means such that a first portion of said product is exposed;
   a first coating means for applying a coating to at least a portion of said first portion of said product;
   a first drying means for drying said coating on said first portion of said product;
   means for advancing said first plurality of carrier plate means to said first coating means and to said first drying means;
   a second plurality of carrier plate means for receiving and retaining a plurality of product;
   transfer means for transferring said product from said first plurality of carrier plate means to said second plurality of carrier plate means such that a second portion of said product is exposed, said transfer means comprises a pair of plate gripper means each having an upper and a lower jaw and each of said jaws being adapted to receive and retain a carrier plate means;
   a second coating means for applying a coating to at least a portion of said second portion of said product;

a second drying means for drying said coating on said second portion of said product;

means for advancing said second plurality of carrier plate means to said second coating means and to said second drying means; and means for unloading said product from said second plurality of carrier plate means.

2. The apparatus of claim 1 wherein said first plurality of carrier plate means are advanced along a first guide means and said second plurality of carrier plate means are advanced along a second guide means.

3. The apparatus of claim 2 wherein said upper jaw and said lower jaw are moveable.

4. The apparatus of claim 3 wherein said transfer means comprises rotation means attached to each pair of plate gripper means, said rotation means being adapted to selectively transfer each pair of plate gripper means back and forth between said first and second guide means.

5. The apparatus of claim 4 wherein each pair of plate gripper means comprises means for selectively opening and closing said upper and lower jaws.

6. The apparatus of claim 5 wherein said opening and closing means comprises cam follower means, said cam follower means being adapted to close each upper and lower jaw to position carrier plate means located in each upper and lower jaw in registration with each other to clamp product between said carrier plate means and to maintain said product clamped therein while said plate gripper means is transferred between guide means.

7. The apparatus of claim 2 wherein said each of said first and second plurality of carrier plate means comprises a plurality of rows of individual product holders and a plate adapted to retain said holders.

8. The apparatus of claim 7 wherein each of said upper and lower jaws being adapted to retain a carrier plate means such that product holders in each plate are aligned with each other.

9. The apparatus of claim 8 wherein each of said upper and lower jaws comprises a plurality of engagement pins movably extendable through openings in said product holders, said pins being adapted to individually engage a product in the holders of a first carrier plate means and transfer the product to the holders of a second carrier plate means aligned with said first carrier plate means.

10. The apparatus of claim 9 wherein said transfer means comprises rotation means attached to each pair of plate gripper means, said rotation means being adapted to selectively transfer each pair of plate gripper means back and forth between said first and second guide means.

11. The apparatus of claim 7 further comprising means for breaking a seal formed between the coating material applied to the product by said first coating means and said holder.

12. The apparatus of claim 11 wherein said seal breaking means comprises a plurality of pairs of engagement pins, a first pin of each pair being extendable through a product holder to contact a product in the holder and lift the product off the holder.

13. The apparatus of claim 12 wherein a second pin of each said pair of engagement pins being spring biased in a close spaced relation to said product in said holder, each said pair of engagement pins sandwiching said product when said product is lifted off said holder, said spring biasing returning said product to said holder when said first pin is retracted from said holder.

14. The apparatus of claim 13 wherein said seal breaking means comprises a cam operated linkage means for extending and retracting said first pin of said pair of engagement pins.

15. The apparatus of claim 7 further comprising a collection means and said unloading means comprises discharge means for causing said coated product to empty into said collection means, and clean out means for cleaning the product holders of product and coating material.

16. The apparatus of claim 15 wherein said discharge means comprises a rotation means for engaging said carrier plate means and rotating said carrier plate means about a pivot point to a discharge position to cause said product to fall into said collection means, and for returning said carrier plate means to its original position on said second guide means.

17. The apparatus of claim 16 wherein said clean out means comprises a plurality of clean out bars adapted to be extended through said product holders while said carrier plate means is in the discharge position.

18. The apparatus of claims 17 wherein said discharge means comprises a cam operated linkage means.

19. The apparatus of claim 18 wherein said clean out means comprises a pair of cam operated linkage means.

20. A method for coating a product comprising:
loading a plurality of uncoated products onto a first plurality of carrier plate means such that a first portion of said product is exposed;
advancing said first plurality of carrier plate means to a first coating means and applying a first coating material on at least a portion of said first portion of said product;
advancing said first plurality of carrier plate means to a first drying means and drying said first coating material;
transferring the coated product from said first plurality of carrier means to a second plurality of carrier means such that a second portion of said product is exposed, said transferring comprises positioning at least one of said first plurality of carrier plate means in registration with at least one of said second plurality of carrier plate means thereby clamping the coated product therebetween as said coated product is transferred;
advancing said second plurality of carrier plate means to a second coating means and applying a second coating material on at least a portion of said second portion of said product;
advancing said second plurality of carrier plate means to a second drying means and drying said second coating material; and
unloading the coated product from said second plurality of carrier plate means.

21. The method of claim 20 further comprising prior to said transferring step breaking a seal formed between the coating material applied to the product by said first coating means and said first plurality of carrier plate means.

22. The method of claim 21 wherein said unloading step comprises discharging said coated product into a collection means, and cleaning the second plurality of carrier plate means of product and coating material.

* * * * *